(12) United States Patent
Thanikachalam (10) Patent No.: US 10,492,911 B2
(45) Date of Patent: Dec. 3, 2019

(54) VENTRICULAR EJECTION DEVICE

(71) Applicant: Mohan Thanikachalam, Newton, MA (US)

(72) Inventor: Mohan Thanikachalam, Newton, MA (US)

(*) Notice: Subject to any disclaimer, the term of this patent is extended or adjusted under 35 U.S.C. 154(b) by 0 days.

(21) Appl. No.: 16/342,822

(22) PCT Filed: Oct. 20, 2017

(86) PCT No.: PCT/US2017/057562
§ 371 (c)(1),
(2) Date: Apr. 17, 2019

(87) PCT Pub. No.: WO2018/075875
PCT Pub. Date: Apr. 26, 2018

(65) Prior Publication Data
US 2019/0231529 A1    Aug. 1, 2019

Related U.S. Application Data

(60) Provisional application No. 62/411,662, filed on Oct. 23, 2016.

(51) Int. Cl.
| | | |
|---|---|---|
| *A61M 1/10* | (2006.01) | |
| *A61M 1/12* | (2006.01) | |
| *A61F 2/24* | (2006.01) | |
| *A61F 2/95* | (2013.01) | |
| *A61L 31/06* | (2006.01) | |

(52) U.S. Cl.
CPC .............. *A61F 2/2487* (2013.01); *A61F 2/95* (2013.01); *A61L 31/06* (2013.01); *A61M 1/10* (2013.01); *A61M 1/1043* (2014.02); *A61M 1/12* (2013.01); *A61M 1/122* (2014.02); *A61F 2210/0014* (2013.01); *A61F 2220/0008* (2013.01); *A61F 2230/0091* (2013.01)

(58) Field of Classification Search
CPC combination set(s) only.
See application file for complete search history.

(56) References Cited

U.S. PATENT DOCUMENTS

| | | | |
|---|---|---|---|
| 7,544,160 B2 * | 6/2009 | Gross | A61F 2/24 600/16 |
| 7,674,222 B2 | 3/2010 | Nikolic et al. | |
| 2012/0035713 A1 | 2/2012 | Lutter et al. | |
| 2012/0316632 A1 | 12/2012 | Gao | |
| 2016/0089238 A1 | 3/2016 | Centola et al. | |

FOREIGN PATENT DOCUMENTS

WO    2011/011642 A2    1/2011

OTHER PUBLICATIONS

International Search Report (Form PCT/ISA/210) dated Feb. 6, 2018 in corresponding International Patent Application No. PCT/US2017/057562.

* cited by examiner

*Primary Examiner* — Paula J Stice
(74) *Attorney, Agent, or Firm* — Pepper Hamilton LLP (57) ABSTRACT

A ventricular ejection device adapted to be delivered percutaneously or surgically in to a ventricle of the heart, and the device comprising of an anchoring stent which is adapted to be fitted along a perimeter to a myocardium of the ventricle, and a recoiling part in physical coupling to the anchoring stent, extends from the perimeter of the anchoring stent to a center of the device, and adapted to extend or recoil based on flow of blood into and out of the ventricle.

16 Claims, 10 Drawing Sheets

VENTRICULAR EJECTION DEVICE

CROSS-REFERENCE TO RELATED APPLICATIONS

This application is a national phase filing under 35 U.S.C. § 371 of International Patent Application Serial No. PCT/US2017/057562, filed on Oct. 20, 2017, which claims priority to U.S. provisional application Ser. No. 62/411,662, filed on Oct. 23, 2016, the entirety of each of which is hereby incorporated by reference.

FIELD

The invention relates to assisted human heart pumping when one or both of the ventricles of the heart do not adequately contract due to issues with the heart muscle. More specifically, the invention relates to assisted heart pumping with respect to systolic heart failure.

BACKGROUND

Deoxygenated blood returns to the heart through the venous system through the right atrium into the right ventricle. The right ventricle then pumps the blood into the lungs to be oxygenated and to the left atrium, then on to the left ventricle. The left ventricle supplies most of the heart's pumping power and pumps the oxygenated blood into systematic circulation.

When the right ventricle fails and does not adequately pump blood into the lungs, the blood backs up in the body's venous system. This causes swelling or congestion in the legs and ankles and swelling within the abdomen such as the gastrointestinal tract and liver and leading to ascites. There are two types of left-sided heart failure, diastolic failure, and systolic failure. In diastolic failure, the left ventricle loses its ability to relax normally, as the heart can't properly fill with blood during the resting period between each beat.

In systolic heart failure, because the left ventricle doesn't squeeze forcefully enough during systole, the heart doesn't pump blood out to the body as well as normal, which leads to a decrease in blood supply to organs, such as the kidneys, leading to organ failure. At the same time, the pressure in the veins of the lung increases, which may cause fluid accumulation in the lungs. This results in shortness of breath and pulmonary edema.

Despite maximal medical therapy, in the majority of patients with right ventricular or systolic left ventricular heart failure there is progressive pathological remodeling of the ventricles and pump failure and, over time, the heart can no longer keep up with the normal demands placed on it to pump blood to the rest of the body. Currently, as these patients progress towards advanced heart failure, the only treatment options are the major surgical procedures such as heart transplant and implantation of mechanical heart pumps, such as ventricular assist devices. One of the major limitations of ventricular assist devices are the need for major surgical procedures and the associated morbidity and costs. Due to complexity of the technology of the ventricular assist devices, there is high incidence of clot formation, damage to blood cells and device failure. Moreover, because of the large power requirement to drive the mechanical pump in the ventricular assist device, there is a need for an external drive line for an external power source, which leads to infections and poor quality of life.

SUMMARY OF THE INVENTION

In one embodiment, a ventricular ejection device can be delivered percutaneously or surgically into a ventricle of the heart. The device includes an anchoring stent and a recoiling part. The anchoring stent is to be fitted along a perimeter to a myocardium of the ventricle. The recoiling part extends from the perimeter of the anchoring stent to a center of the device. The recoiling part is in physical coupling with the anchoring stent. The recoiling part is adapted to be in a normal position along a plane of the anchoring stent, a first extended position, or a second extended position. When the blood enters the ventricle during a diastolic phase of a cardiac cycle, the recoiling part is adapted to move into the first extended position. The recoiling part moves to a second extended position by further extending from the first extended position. When the heart moves from diastolic phase to the systolic phase, and is in an isovolumetric contraction part of the systolic phase, the recoiling part extends further from the first extended position to the second extended position and during the end of the systolic phase the recoiling part is adapted to recoil to the normal position and to eject the blood out of the ventricle.

The anchoring stent can also be fitted along the myocardium of the ventricle to form a seal along walls of the ventricle, such that the ventricular ejection device makes a division between volumes of a cavity of the ventricle of the heart on opposing sides of the recoiling part.

In one embodiment, the recoiling part can have an elastic or flexible membrane, and a spring. The spring extends from the anchoring stent. The membrane extends from the anchoring stent to cover the spring of the recoiling part, such that the anchoring stent and the spring, along with the membrane forms a disc geometry when the recoiling part is in the normal position.

In one embodiment, the anchoring stent and the spring is made of a single wire such that the wire forms the anchoring stent, and further extends from the stent towards the center in a helical manner to form the spring of the recoiling part. The wire also forms anchoring elements in the anchoring stent such that there are set of anchoring elements along the anchoring stent. The anchoring elements anchor the device to the myocardium to prevent migration of the device.

In one embodiment, the anchoring stent is flexible, and can expand or compress. The anchoring stent is in a collapsed position while being delivered into the ventricle of the heart and when deployed it expands radially outward to a first anchoring position to fit the anchoring stent along the perimeter to the myocardium of the ventricle. Further, the anchoring elements are adapted to bend radially outward further forming an outward angle between forty-five to sixty degrees with respect to the plane of the recoiling part in the normal position, such that the anchoring stent achieves a second anchoring position.

Further benefits, goals and features of the present invention will be described by the following specification and the attached figures, in which components of the invention are exemplarily illustrated. Components of the devices and method, which match at least essentially with respect to their function, can be marked with the same reference sign, wherein such components do not have to be marked or described in all figures.

DETAILED DESCRIPTION

The embodiments are described herein for illustrative purposes and are subject to many variations. It is understood that various omissions and substitutions of equivalents are contemplated as circumstances may suggest or render expedient, but are intended to cover the application or implementation without departing from the spirit or scope of the present invention. Further, it is to be understood that the phraseology and terminology employed herein are for the purpose of the description and should not be regarded as limiting. Any heading utilized within this description is for convenience only and has no legal or limiting effect.

The terms "a" and "an" herein do not denote a limitation of quantity, but rather denote the presence of at least one of the referenced item.

A percutaneously or surgically installed ventricular ejection device which assists the human heart in pumping blood out of either the right ventricle or the left ventricle of the heart is described herein. For purposes of understanding the invention, the embodiments of the ventricular ejection device are disclosed where it is assisting the human heart during systolic phase of the cardiac cycle to pump out the blood from the left ventricle of the heart.

FIGS. 1A-1D show a ventricular ejection device 1 from the top view and the front view. The ventricular ejection device 1 has two parts, an anchoring stent 4 and a recoiling part 5. When the ventricular ejection device 1 is deployed into a ventricle of the heart, the anchoring stent 4 forms a perimeter of the device 1 and secures the ventricular ejection device 1 to a myocardium of the ventricle. This helps to keep the device 1 intact in the ventricle and enable it to sustain blood pressure during diastolic phase, and systolic phase. If the device 1 is not properly anchored, and therefore not securely affixed to the myocardium, it shall create issues with instability of the device 1 in the heart and require undesired intervention into the heart for re-placement of the device 1.

The recoiling part 5 is in physical coupling to the anchoring stent 4, so as to retain the blood, when the blood enters into the ventricle of the human heart. The recoiling part 5 can include a membrane 12 which extends from the perimeter of the anchoring stent 4 to a center of the device 1. Hence, the membrane 12 forms a blood impermeable barrier which separates an upper cavity of the ventricle from a lower portion.

Figure 1A:
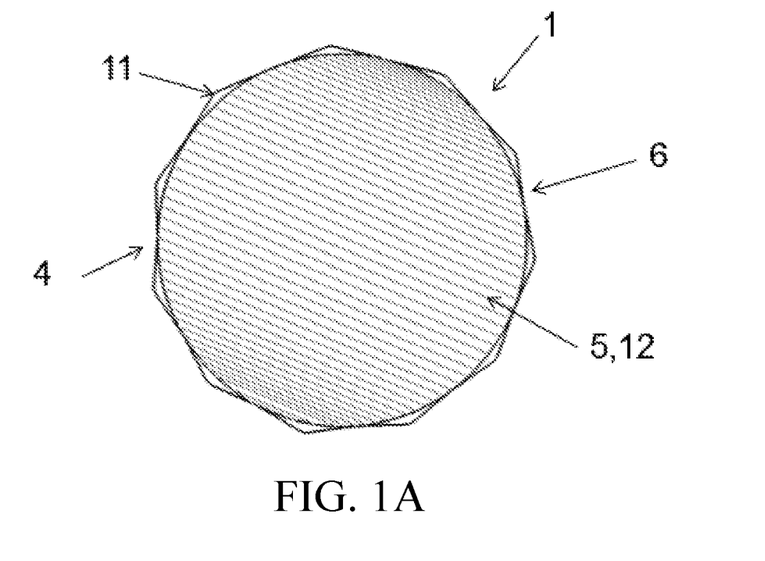
FIG. 1A illustrates a top view of a ventricular ejection device when a recoiling part of the device is in a normal position.
Figure 1B:
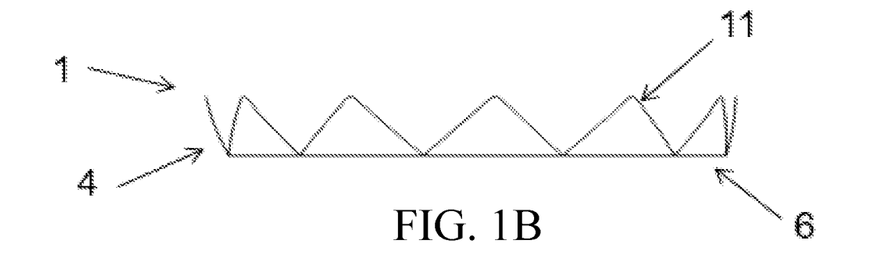
FIG. 1B illustrates a front view of the ventricular ejection device when the recoiling part of the device is in the normal position.
Figure 1C:
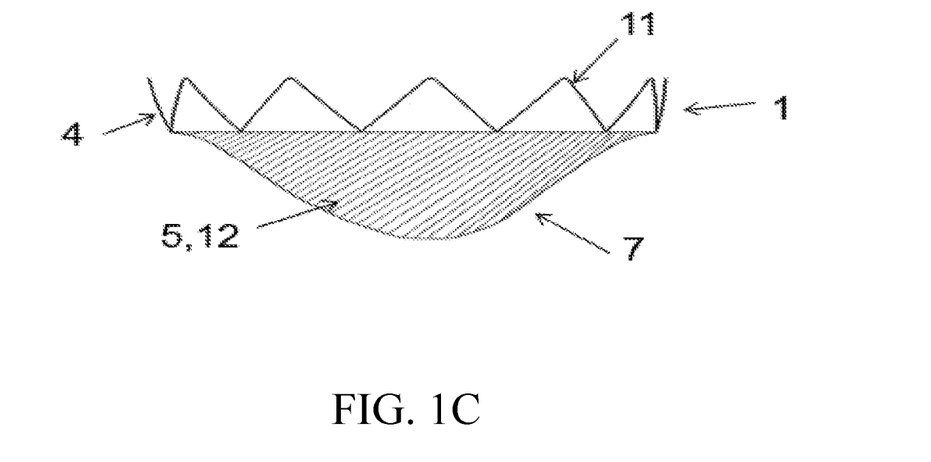
FIG. 1C illustrates a front view of the ventricular ejection device when the recoiling part of the device is in a first extended position.
Figure 1D:
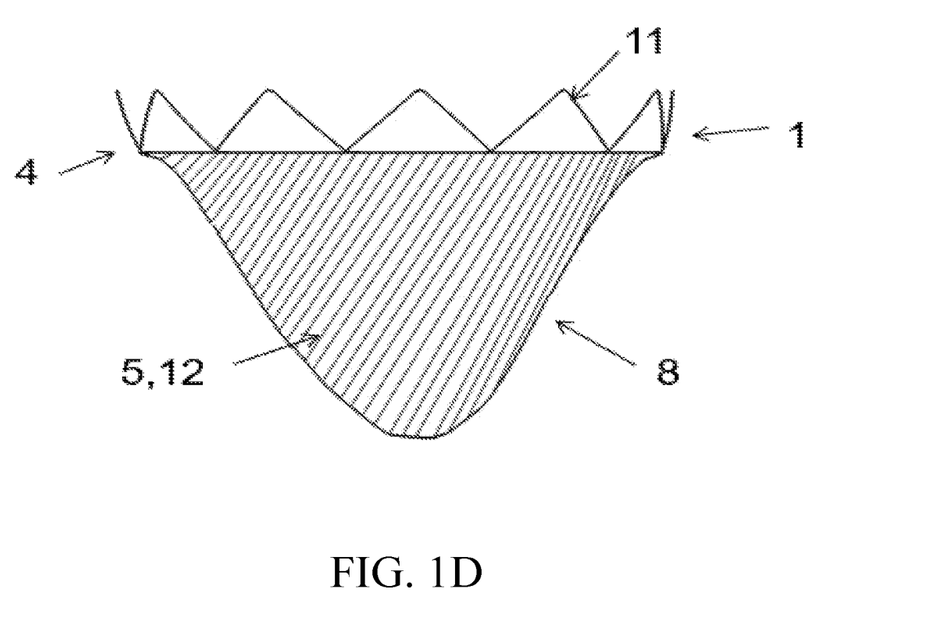
FIG. 1D illustrates a front view of the ventricular ejection device when the recoiling part of the device is in a second extended position

In operation, the recoiling part 5 extends or recoils based on flow of blood into and out of the ventricle. When the blood enters the ventricle of the heart, the recoiling part 5 extends. More specifically, when the blood enters the ventricle during a diastolic phase of a cardiac cycle, the recoiling part 5 moves into a first extended position 7, as shown in FIG. 1C. When the heart moves from diastolic phase to the systolic phase, and is in an isovolumetric contraction part of the systolic phase, the recoiling part 5 extends further from the first extended position 7 to the second extended position 8 as shown in FIG. 1D. At the end of the systolic phase the recoiling part 5 recoils to the normal position 6 as shown FIG. 1A and 1B and ejects the blood out of the ventricle.

In one embodiment, the anchoring stent 4 is adapted to be fitted along the myocardium of the ventricle, just below the papillary muscles of the ventricle so as to form a seal along walls of the ventricle. This helps to provide a division between volumes of a cavity of the ventricle of the heart on opposing sides of the recoiling part 5. This creates an empty zone of expansion below the device 1 for the recoiling part 5 to expand and recoil.

Figure 5A:
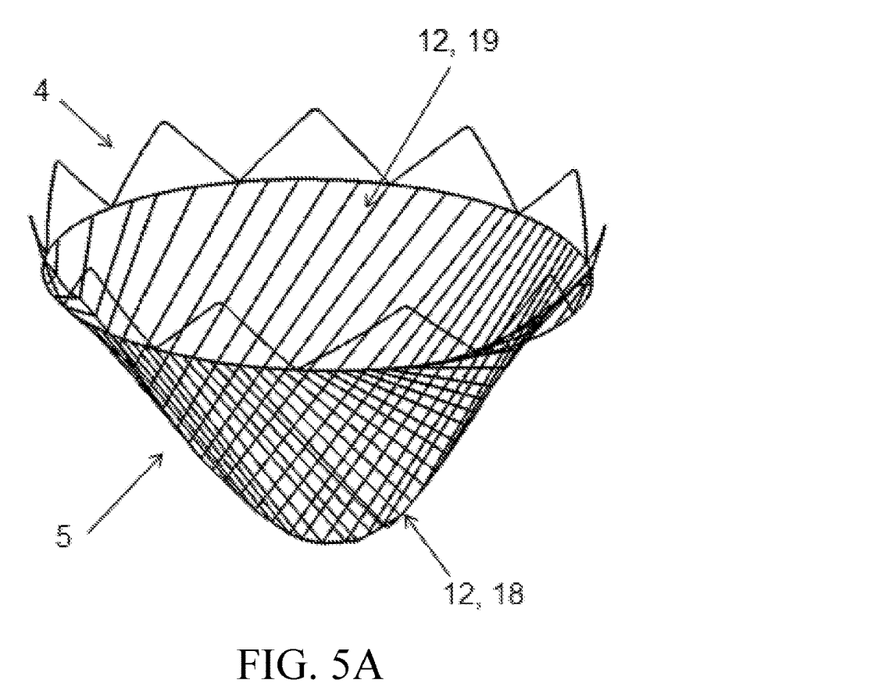
FIG. 5A illustrates the ventricular ejection device made from the single wire, with a spring and two elastic or flexible membrane, such that the spring is sandwiched between the two membranes.
Figure 5B:
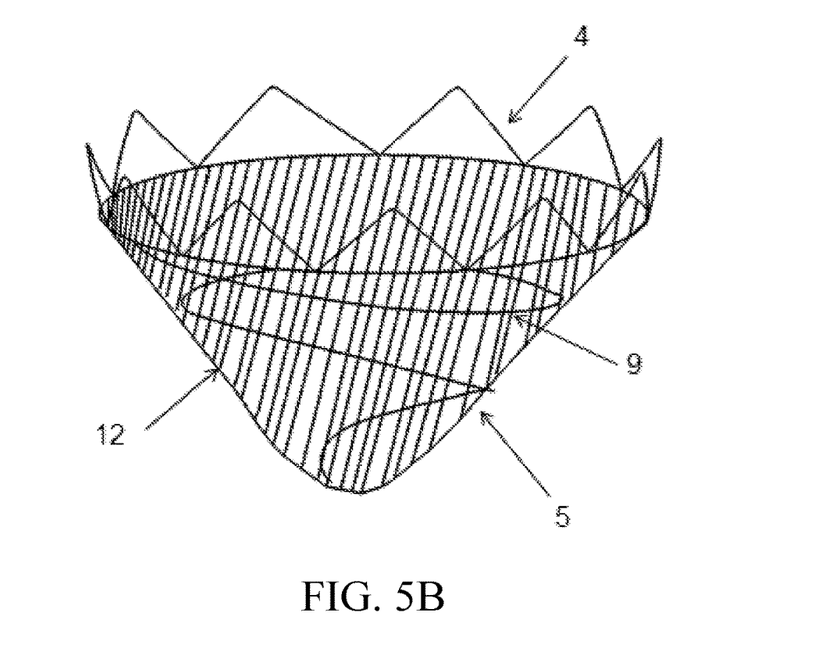
FIG. 5B illustrates the ventricular ejection device made from the single wire, with the spring and one elastic or flexible membrane, such that membrane is placed above the spring.
Figure 5C:
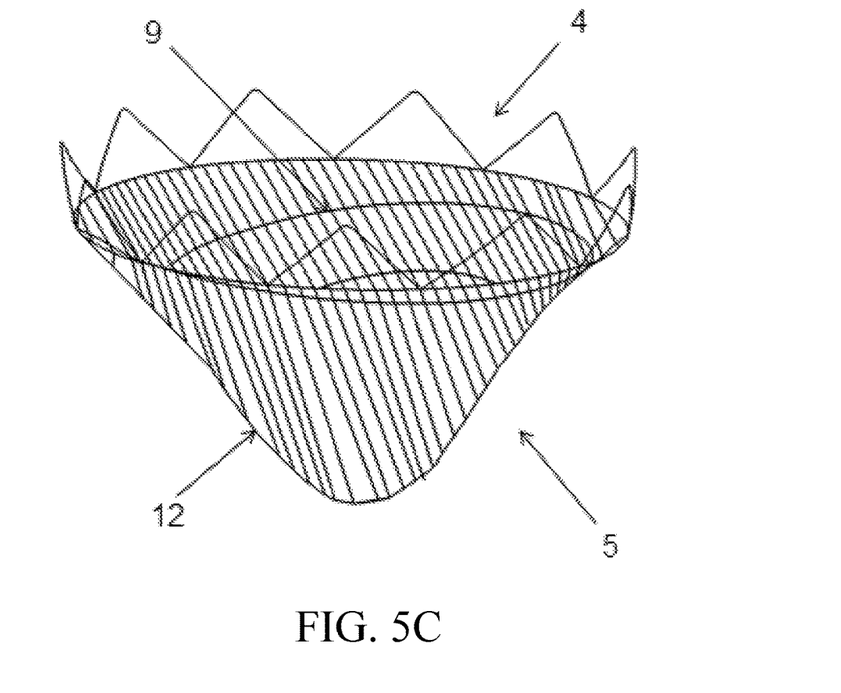
FIG. 5C illustrates the ventricular ejection device made from the single wire, with the spring and one elastic or flexible membrane, such that membrane is placed below the spring.
Figure 6A:
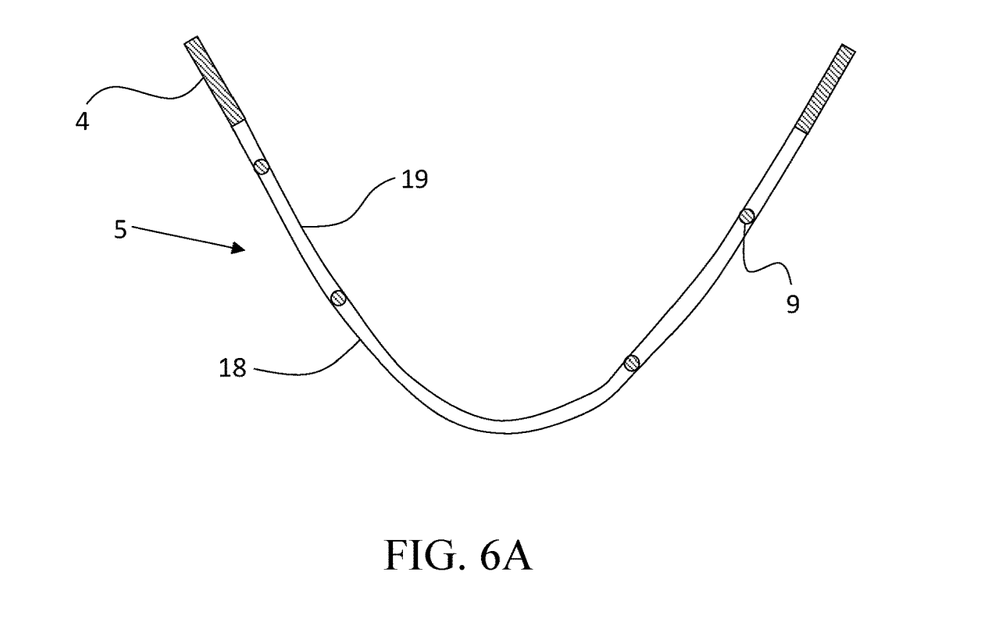
FIG. 6A is a cross-sectional view of the ventricular ejection device of FIG. 5A.
Figure 6B:
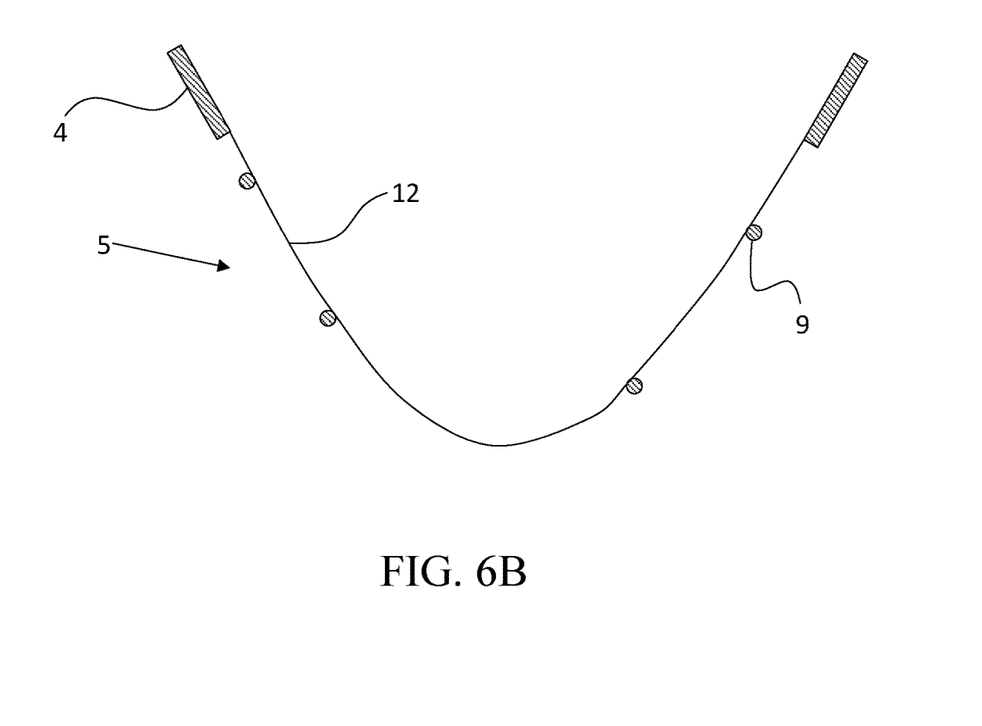
FIG. 6B is a cross-sectional view of the ventricular ejection device of FIG. 5B.
Figure 6C:
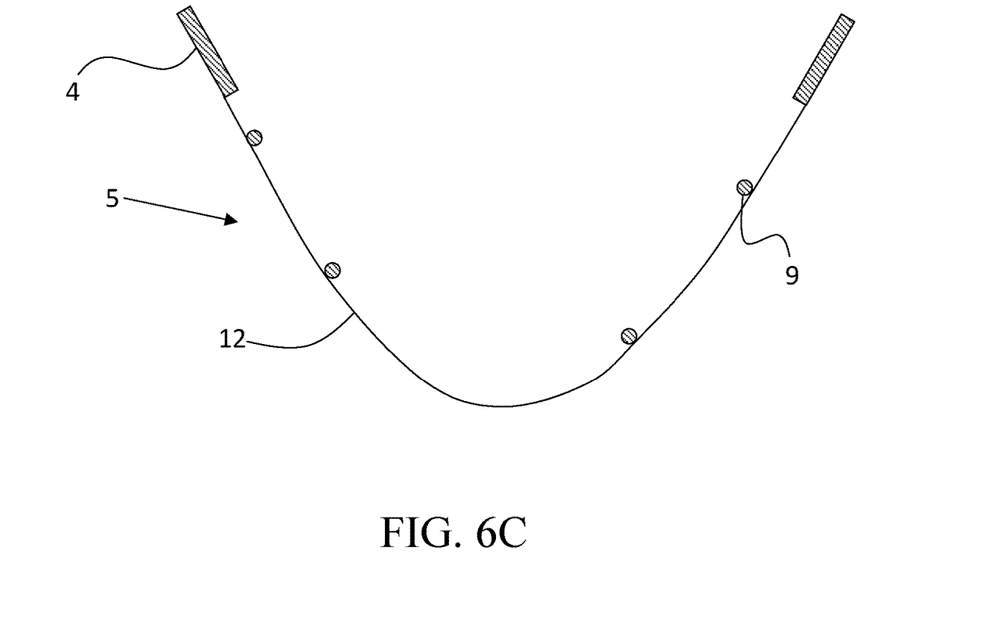
FIG. 6C is a cross-sectional view of the ventricular ejection device of FIG. 5C.

In one embodiment, the recoiling part 5 includes an elastic membrane 12 and a spring 9. The spring 9 helps in augmenting the extendibility and recoiling efficiency of the recoiling part 5. The spring 9 can be placed above membrane 12, as shown in FIGS. 5C and 6C or below the membrane 12, as shown in FIGS. 5B and 6B. In another alternate embodiment, the ventricular ejection device 1 is provided with two membranes 12, such that the spring 9 is sandwiched between the two membranes 12, as shown in FIGS. 5A and 6A. Providing two membranes 12 and placing the spring 9 in between them further strengthens the recoiling part 5 physically, and provides for still better efficiency in recoiling and extendibility of the recoiling part 5.

In one embodiment, the membrane 12 is made of polyethylene material, such as Expanded polytetrafluoroethylene, or (ePTFE,), and other polymers such as silicones, polyvinyl chloride, polyurethanes, polylactides, collagen, gelatin, elastin, silk, and polysaccharides. The membrane 12 can be affixed to the anchoring stent 4 by any appropriate means. For example, the membrane 12 can be bonded to the anchoring stent 4. The membrane 12 can further be affixed to the spring 9 by bonding or other appropriate means.

Figure 2:
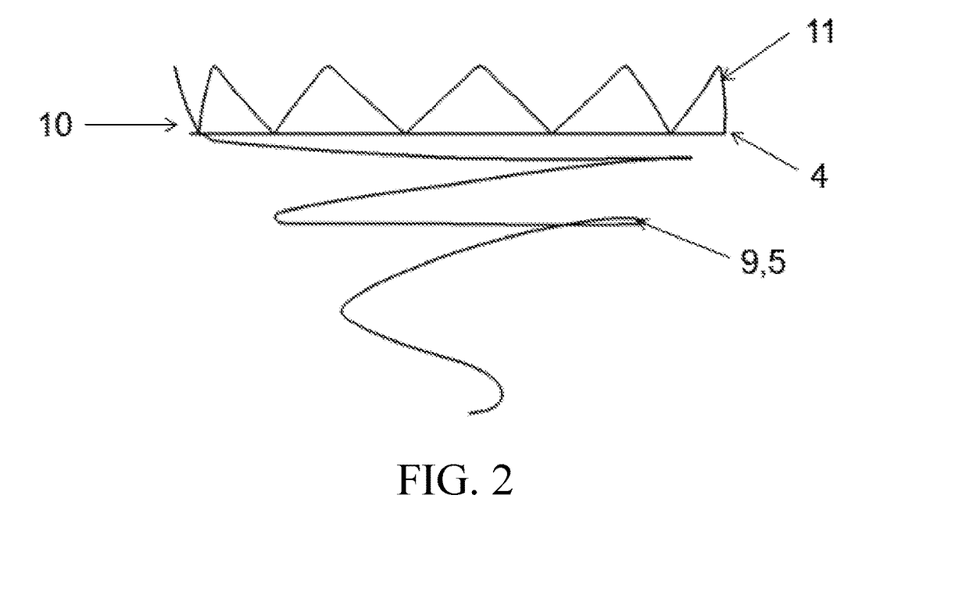
FIG. 2 illustrates a front view of the ventricular ejection device made from a single wire.

FIG. 2 shows a front view of the ventricular ejection device 1 made from a single wire 10. The single wire 10 forms both the anchoring stent 4 and the spring 9 such that the wire 10 forms the anchoring stent 4, and further extends from the stent towards the center in a helical manner to form the spring 9 of the recoiling part 5. Also, the wire 10 forms anchoring elements 11 in the anchoring stent 4 such that there is a set of anchoring elements 11 along the anchoring stent 4.

In one implementation of the invention, the straight wire 10 is initially made into a zig zag to form the anchoring elements 11. The zig zag part of the wire 10 makes a circle and one end of the wire 10 ends as a hook, which hooks on to another bent portion at the other end of the wire 10 to form a complete circle and makes anchoring elements 11 of the anchoring stent 4. The other end of the wire 10 which makes a sharp bend continues to make a coil and thus forms the helical spring 9 of the recoiling part 5.

Making the device 1 from a single wire 10 without welded points prevents the device 1 from fracturing and increases the durability of the device 1. The various combinations of the parameters of the geometry including number of anchoring elements 11, the height of the anchoring elements 11, the thickness of the wire 10, and the stiffness of the wire 10 determines the radial force, which acts to force the anchoring stent 4 radially outward into the myocardium. These parameters are optimized to provide adequate radial force to prevent device 1 from migrating under a wide range of intra ventricular pressures, from 0 to 250 mmhg. In another implementation of the invention, the anchoring elements 11 of the anchoring stent 4 is to be made in such a way that the anchoring elements 11 form an outward angle between forty-five to sixty degrees once deployed, which in addition to the radial force, enables better anchoring of the ventricular ejection device 1 into the myocardium and prevents migration of the device 1.

In one embodiment, the wire 10 is made of a shape memory alloy, such as such as nickel-titanium alloy (e.g., Nitinol). Alternatively, the wire 10 can be made of any appropriate material, for example stainless steel, gold, titanium, cobalt-chromium, tantalum, and polymers.

In one embodiment, the number of coils ranges from 3 to 6 of the spring 9, and thickness of the wire 10 ranges from 0.28 to 0.40 mm, and thickness of the membrane ranges from 0.12 mm to 0.16 mm. The number of coils of the spring 9, the thickness of the wire 10 and its material properties (e.g., stiffness) determines the recoil force of the recoiling part 5, and thus cardiac ejection. In another implementation, membrane 12 is used along with spring 9 of the wire 10 either above the spring 9, or outside of the spring 9, or sandwiching the spring 9 between two membranes 12. In such scenario, the thickness and property of the membrane 12 also determines the recoil force. The design parameters of the coil and membrane 12 are optimized to provide adequate recoil force and cardiac ejection FIGS. 5A-5C show different ways the spring 9 and the membrane 12 can be placed with respect to each other, when the anchoring stent 4 and the spring 9 of the recoiling part 5 is made of single wire. In FIG. 5A, the ventricular ejection device 1 is provided with two membranes 12, a first membrane 18, and a second membrane 19, such that the spring (shown in FIG. 6A) is sandwiched between the first membrane 18 and the second membrane 19. In FIGS. 5B and 6B, the membrane 12 is shown placed above the spring 9, and in FIGS. 5C and 6C, the membrane is shown placed below the spring 9.

Figure 3A:
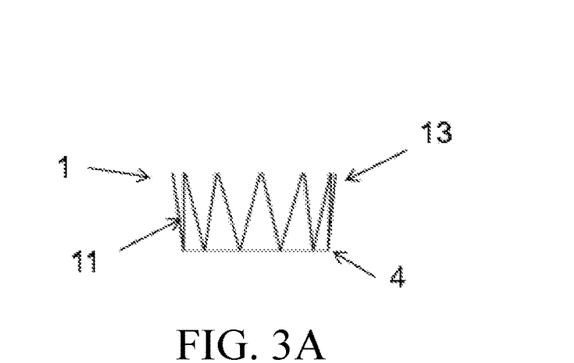
FIG. 3A illustrates a front view of the ventricular ejection device in the crimped form when it is under delivery, and not yet deployed.

The design parameters of the anchoring elements 11, spring 9 and membrane 12 are to be optimized to enable the anchoring elements 11, spring 9 and membrane 12 to be crimped into a disc geometry with a lesser diameter, as shown in FIG. 3A. This enables the device 1 to be loaded in to a catheter, which can pass through a peripheral artery and enable the device 1 to be delivered percutaneously into the ventricular cavity. In one embodiment, the parameters of anchoring elements 11, spring 9 and membrane 12 should be optimized to keep the crimped diameter to less than 7 mm.

Figure 3B:
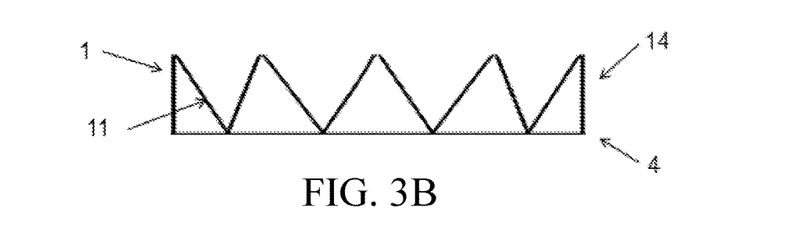
FIG. 3B illustrates a front view of the ventricular ejection device when the device is deployed and the anchoring stent is in a first anchoring position.

The anchoring stent 4 is flexible, and can be collapsed or expanded, which enables the device 1 to be in the collapsed position 13 while being delivered into the ventricle of the heart. However, when the catheter is withdrawn, the anchoring stent 4 expands radially outward to expand the perimeter of the anchoring stent 4, and to be in a first anchoring position 14, as shown in FIG. 3B. This helps to fit the anchoring stent 4 along the perimeter to the myocardium of the ventricle.

Figure 3C:
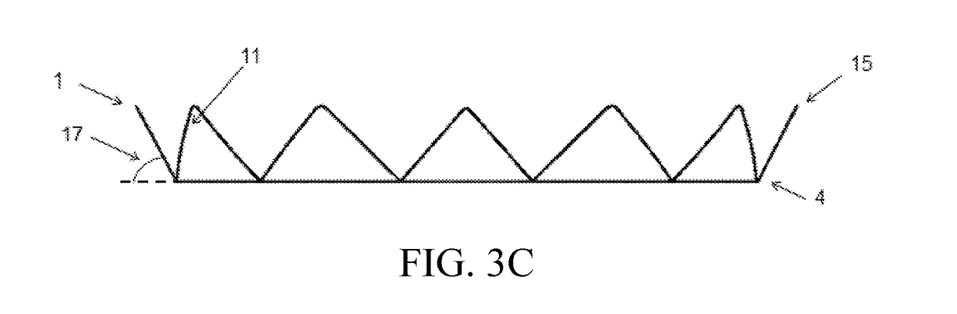
FIG. 3C illustrates a front view of the ventricular ejection device when the device is deployed and the anchoring stent is in a second anchoring position.

In furtherance, the anchoring elements 11 are adapted to bend radially outward further forming an outward angle 17 between forty-five to sixty degrees with respect to the plane of the recoiling part 5 in normal position 6, as shown in FIG. 3C. This helps to achieve a second anchoring position 15 and anchor the device 1 to the myocardium to prevent migration of the device 1. It is to be noted that in the first anchoring position 14, the perimeter of the anchoring stent 4 is expanded. While in the second anchoring position 15, the perimeter of the anchoring stent 4 remains same as of in the first anchoring position, and only the anchoring elements 11 bends radially outwards in the angular fashion.

FIGS. 4A-4E show delivery, deployment and functioning of the ventricular ejection device 1 inside a ventricle 2 of the heart 3.

Figure 4A:
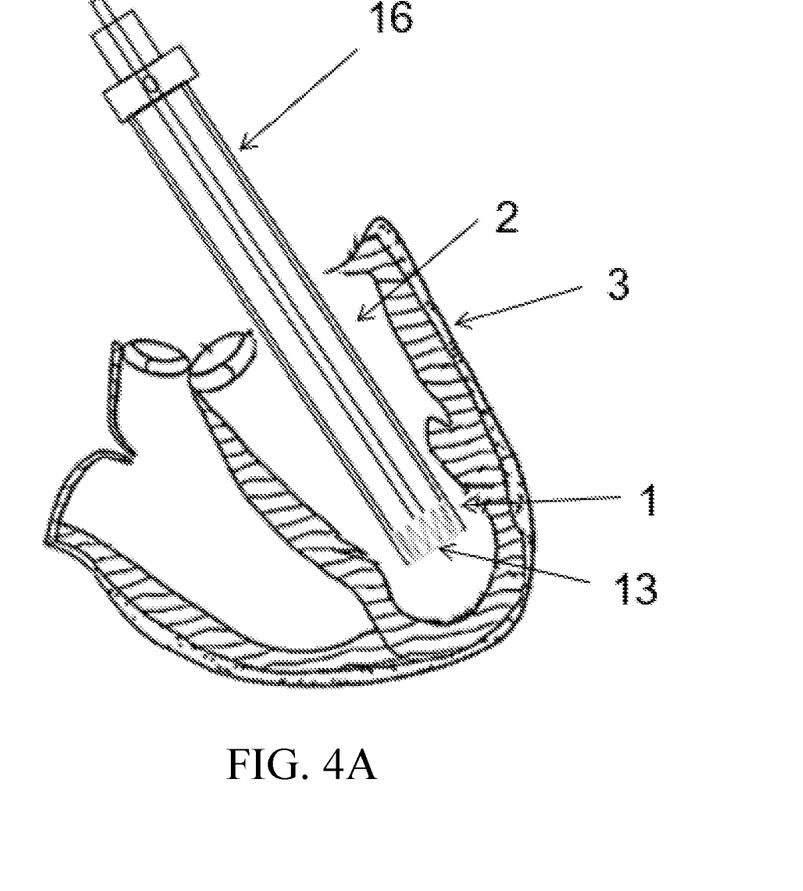
FIG. 4A illustrates the ventricular ejection device in a collapsed form in a catheter, while the catheter is delivering the device in a ventricle of a heart.
Figure 4B:
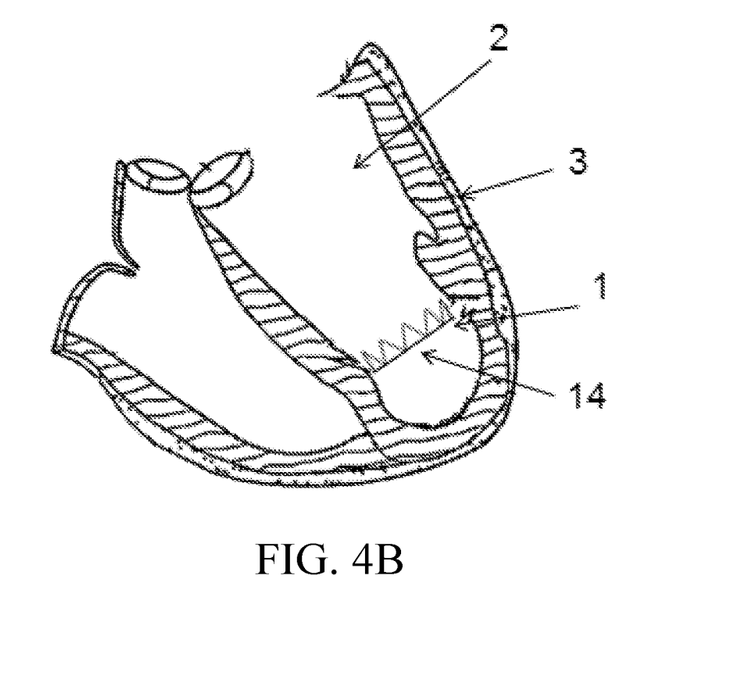
FIG. 4B illustrates the ventricular ejection device after being released in the ventricle of the heart for being deployed in the ventricle.

In FIG. 4A, a catheter 16 is shown carrying the ventricular ejection device 1 in package form into a ventricle 2 of the heart 3. The device 1 is in crimped form or collapsed position, so as to fit in the catheter 16 carrying the device 1. When in the collapsed state, a portion of the device, such as the anchoring stent 4, can store elastic energy. Once the catheter 16 reaches inside the ventricle 2 at an appropriate location, as considered appropriate by the user of the catheter 16, the device 1 is released from the catheter 16 to be deployed in the ventricle 2, as shown in FIG. 4B. While being deployed, the elastic energy stored in the anchoring stent 4 causes the device 1 to expand radially outward to a first anchoring position 14 to fit the anchoring stent 4 along the perimeter to the myocardium of the ventricle 2.

Figure 4C:
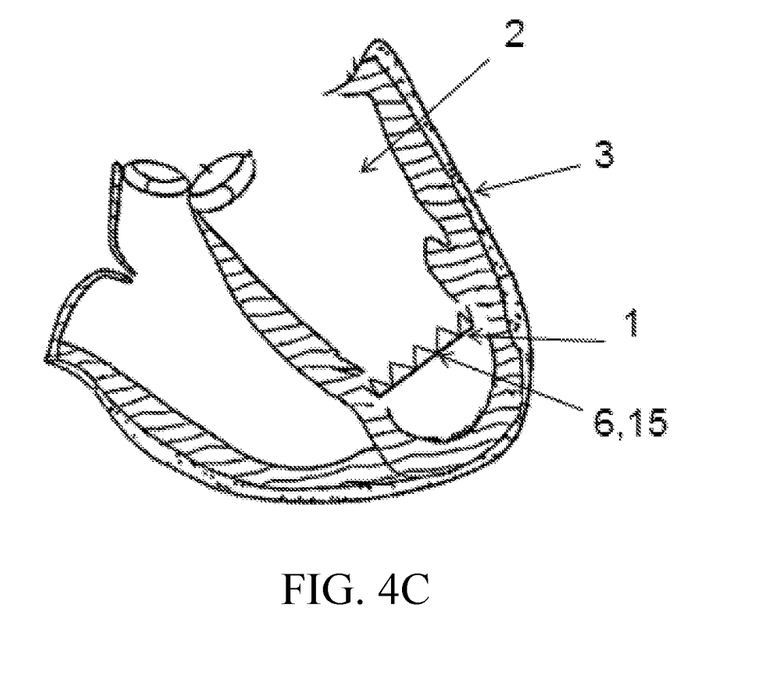
FIG. 4C illustrates the ventricular ejection device anchored to a myocardium of the ventricle.

In furtherance, the anchoring elements 11 of the anchoring stent 4 bends to achieve a second anchoring position 15, and anchors the device 1 to the myocardium to prevent migration of the device 1, as shown in FIG. 4C.

Figure 4D:
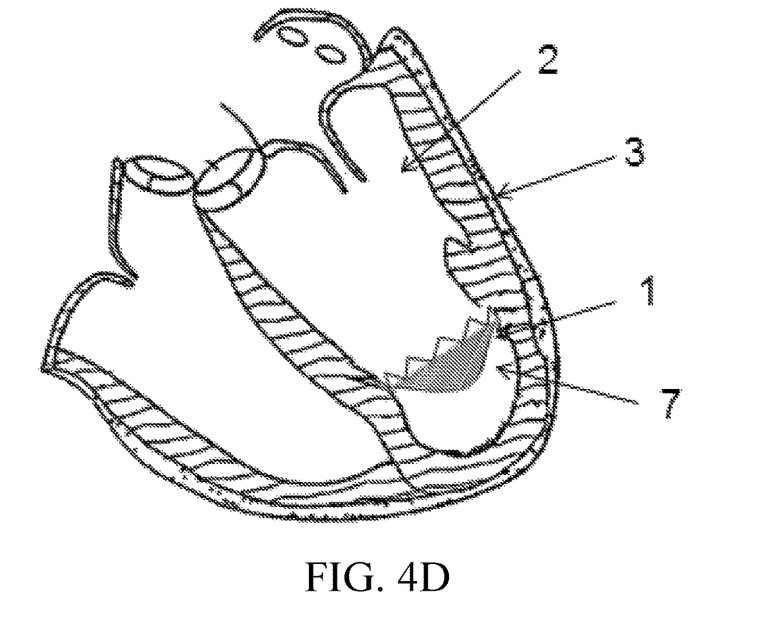
FIG. 4D illustrates the ventricular ejection device during end of diastolic phase of the cardiac cycle.
Figure 4E:
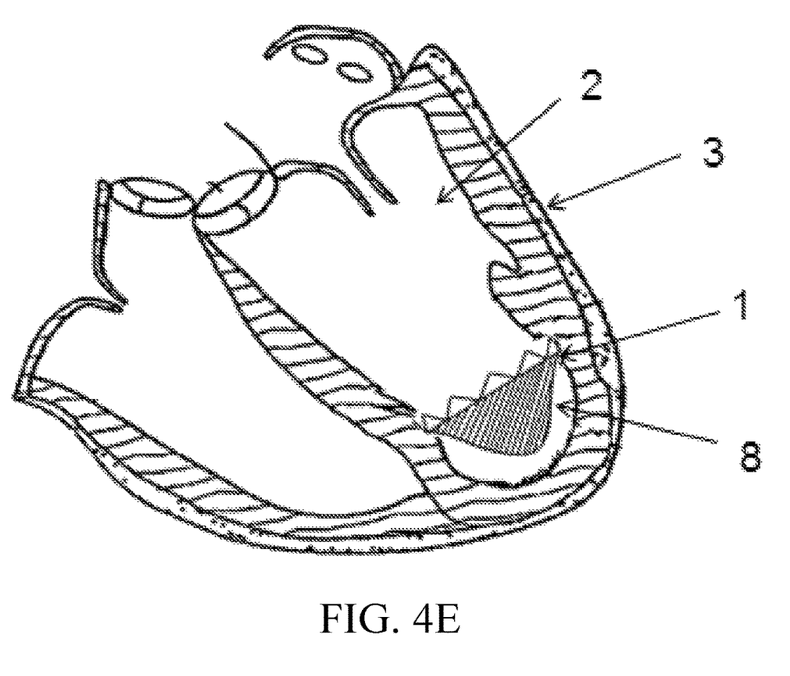
FIG. 4E illustrates the ventricular ejection device during an isovolumetric contraction part of the systolic phase of the cardiac cycle.

Thereafter, the ventricular ejection device 1 starts cooperating with the cardiac cycle of heart 3, such that in the diastolic phase when the blood enters the ventricle 2, the recoiling part 5 of the device 1 extends to the first extended position 7, as shown in FIG. 4D. Further, when the heart 3 moves from diastolic phase to the systolic phase, and is in an isovolumetric contraction part of the systolic phase, the recoiling part 5 extends further from the first extended position 7 to the second extended position 8, as shown in FIG. 4E. This helps to retain the maximum blood flow into the ventricle 2 during the cardiac cycle. Thereafter, during the end of the systolic phase the recoiling part 5 recoils to the normal position 6 and ejects the blood out of the ventricle 2.

In this way, the ventricular ejection device 1 assists in proper functioning of the compromised ventricle 2 during the cardiac cycle.

The invention claimed is:

1. A ventricular ejection device adapted to be delivered percutaneously or surgically into a ventricle of a heart, the ventricular ejection device comprising:
    an anchoring stent which is adapted to be fitted along a perimeter to a myocardium of the ventricle; and
    a recoiling part in physical coupling to the anchoring stent, the recoiling part extending from the perimeter of the anchoring stent to a center of the device, and adapted to extend or recoil based on flow of blood into and out of the ventricle.

2. The ventricular ejection device according to claim 1, wherein the recoiling part is adapted to be in a normal position along a plane of the anchoring stent.

3. The ventricular ejection device according to claim 2, wherein the anchoring stent comprises anchoring elements, and when the anchoring stent is in first anchoring position, the anchoring elements are adapted to bend radially outward further forming an outward angle between forty-five to sixty degrees with respect to the plane of the recoiling part in the normal position to achieve a second anchoring position and anchor the device to the myocardium to prevent migration of the device.

4. The ventricular ejection device according to claim 1, wherein the recoiling part is adapted to be in a first extended position, such that when the blood enters the ventricle during a diastolic phase of a cardiac cycle, the recoiling part is adapted to move into the first extended position.

5. The ventricular ejection device according to claim 1, wherein the recoiling part is adapted to be in a second extended position by further extending the recoiling part from the first extended position, such that when the heart moves from diastolic phase to the systolic phase, and is in an isovolumetric contraction part of the systolic phase, the recoiling part extends further from the first extended position to the second extended position and during the end of the systolic phase the recoiling part is adapted to recoil to the normal position and to eject the blood out of the ventricle.

6. The ventricular ejection device according to claim 1, wherein the anchoring stent is adapted to be fitted along the myocardium of the ventricle and to form a seal along walls of the ventricle, such that the ventricular ejection device makes a division between volumes of a cavity of the ventricle of the heart on opposing sides of the recoiling part.

7. The ventricular ejection device according to claim 1, wherein the recoiling part comprises a spring extending from the anchoring stent.

8. The ventricular ejection device according to claim 7, wherein the spring is a helical spring.

9. The ventricular ejection device according to claim 8, wherein the anchoring stent and the spring are made of a single wire such that the wire forms the anchoring stent, and further extends from the stent towards the center in a helical manner to form the spring of the recoiling part.

10. The ventricular ejection device according to claim 9, the wire further forms anchoring elements in the anchoring stent such that there are set of anchoring elements along the anchoring stent.

11. The ventricular ejection device according to claim 9, wherein the wire is made of a shape memory alloy.

12. The ventricular ejection device according to claim 7, wherein the recoiling part comprises at least one elastic or flexible membrane extending from the anchoring stent to cover the spring of the recoiling part, such that the anchoring stent and the spring, along with the membrane forms a disc geometry when the recoiling part is in the normal position.

13. The ventricular ejection device according to claim 12, wherein the membrane extends on either side of the spring of the recoiling part.

14. The ventricular ejection device according to claim 12, wherein the membrane extends on both sides of the spring of the recoiling part, such that the spring is embedded between the two membranes.

15. The ventricular ejection device according to claim 12, wherein the membrane is made of polyethylene material.

16. The ventricular ejection device according to claim 1, wherein the anchoring stent is flexible, and adapted to collapse or expand, wherein the anchoring stent is in a collapsed position while being delivered into the ventricle of the heart and when deployed it expands radially outward to a first anchoring position to fit the anchoring stent along the perimeter to the myocardium of the ventricle.

\* \* \* \* \*